US008817269B2

(12) United States Patent
Tumlinson

(10) Patent No.: US 8,817,269 B2
(45) Date of Patent: Aug. 26, 2014

(54) FIZEAU REFERENCE ARM USING A CHIRPED FIBER BRAGG GRATING

(75) Inventor: Alexandre R. Tumlinson, San Leandro, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 166 days.

(21) Appl. No.: 13/457,297

(22) Filed: Apr. 26, 2012

(65) Prior Publication Data
US 2012/0274943 A1 Nov. 1, 2012

Related U.S. Application Data

(60) Provisional application No. 61/479,329, filed on Apr. 26, 2011.

(51) Int. Cl.
*G01B 9/02* (2006.01)

(52) U.S. Cl.
USPC .......................................... 356/479; 356/451

(58) Field of Classification Search
USPC .......... 356/478, 479, 482, 497; 351/210, 221, 351/205
See application file for complete search history.

(56) References Cited

U.S. PATENT DOCUMENTS

| 5,718,738 | A | 2/1998 | Kohnke et al. |
| 7,057,738 | B2 | 6/2006 | Millerd et al. |
| 2007/0051882 | A1* | 3/2007 | Childers ................. 250/227.14 |
| 2008/0034866 | A1* | 2/2008 | Kilic et al. ................. 73/514.26 |
| 2010/0091265 | A1* | 4/2010 | Franz ............................. 356/51 |
| 2010/0128276 | A1* | 5/2010 | De Groot et al. ............ 356/450 |

FOREIGN PATENT DOCUMENTS

WO 2007/002969 A1 1/2007

OTHER PUBLICATIONS

Caucheteur et al., "All-Fiber Tunable Optical Delay Line", Optics Express, vol. 18, No. 3, Feb. 1, 2010, pp. 3093-3100.
Choi et al., "All-Fiber Variable Optical Delay Line for Applications in Optical Coherence Tomography: Feasibility Study for a Novel Delay Line", Optics Express, vol. 13, No. 4, Feb. 21, 2005, pp. 1334-1345.
Choi et al., "Strained Chirped Fiber Bragg Gratings Based All-Fiber Variable Optical Delay Line for Optical Coherence Tomography", Optical and Quantum Electronics, vol. 37, 2005, pp. 1263-1276.
Hofer et al., "Dispersion Encoded Full Range Frequency Domain Optical Coherence Tomography", Optics Express, vol. 17, No. 1, Jan. 5, 2009, pp. 7-24.
Karim et al., "Numerical Analysis of Raised Cosine Sampled Chirped Bragg Grating for Dispersion Compensation in Dense Wavelength Division Multiplexing Systems", International Journal of Communications, vol. 3, No. 1, 2009, pp. 9-16.
Oldenburg et al., "Fast-Fourier-Domain Delay Line for in vivo Optical Coherence Tomography with a Polygonal Scanner", Applied Optics, vol. 42, No. 22, Aug. 1, 2003, pp. 4606-4611.

(Continued)

Primary Examiner — Kara E. Geisel
Assistant Examiner — Dominic J Bologna
(74) Attorney, Agent, or Firm — Morrison & Foerster LLP

(57) ABSTRACT

An improved interferometer measurement system is presented. In a preferred embodiment, a chirped fiber Bragg grating is used as a reference surface in a Fizeau interferometer arrangement for optical coherence tomography imaging of the eye. The grating creates a virtual reference surface near the sample and allows for a relatively short reference arm while maintaining close to zero delay interference conditions.

13 Claims, 2 Drawing Sheets

(56) References Cited

OTHER PUBLICATIONS

Sharma et al., "All-Fiber Common-Path Optical Coherence Tomography: Sensitivity Optimization and System Analysis", IEEE Journal of Selected Topics in Quantum Electronics, vol. 11, No. 4, Jul./Aug. 2005, pp. 799-805.

Tan et al., "In-Fiber Common-Path Optical Coherence Tomography Using a Conical-Tip Fiber", Optics Express, vol. 17, No. 4, Feb. 16, 2009, pp. 2375-2384.

Tumlinson et al., "Endoscope-Tip Interferometer for Ultrahigh Resolution Frequency Domain Optical Coherence Tomography in Mouse Colon", Optics Express, vol. 14, No. 5, Mar. 6, 2006, pp. 1878-1887.

Yang et al., "Amplification of Optical Delay by Use of Matched Linearly Chirped Fiber Bragg Gratings", Optics Letters, vol. 29, No. 7, Apr. 1, 2004, pp. 685-687.

\* cited by examiner

FIZEAU REFERENCE ARM USING A CHIRPED FIBER BRAGG GRATING

PRIORITY

This application claims priority to U.S. Provisional Application Ser. No. 61/479,329, filed Apr. 26, 2011, hereby incorporated by reference.

TECHNICAL FIELD

One or more embodiments of the present invention generally relate to improvements in interferometric measurement systems. In particular, it is an aspect of the present invention to use a chirped Bragg grating as a reference 'surface' in a Fizeau interferometer configuration. The grating allows one to use a comparatively short reference arm in a Fizeau interferometer while maintaining close to zero delay interference conditions.

BACKGROUND

Typically one thinks of the key aspect of interferometer design as an attempt to match the path lengths of the sample and reference arms. In the time domain, one only observes an interference envelope when these two paths are closely matched. The length of the reference arm was typically modulated to correspond to various depths within the tissue. In state of the art frequency domain systems, the reference is usually placed at fixed distance relative to the tissue and the maximum difference between the two arms is limited by the sampling of k-space. With a finer line width and greater number of samples, one can observe a greater distance away from the zero delay.

The attempt to match path lengths is only one aspect of the actual problem one is trying to solve when performing white light interferometry. The problem can be more generically stated: In order to observe interference between the two paths, the phase difference between the two paths must vary across the spectrum in a manner which can be observed by a detector. When the light from the reference path interferes with the light from the sample path, the phase of interference may be detected if:

1. The optical bandwidth simultaneously superimposed upon a location of the detector is sufficiently narrow to produce an interference that is substantially invariant during the measurement time (coherence length).
2. The phase difference from optical frequency to optical frequency changes at a slow enough rate that it may be sampled by the detector.

For spectrally resolved detection, the rate of phase difference across the spectrum must vary slowly enough that the phase difference is essentially constant across each detector element. For temporally resolved detection, the rate of phase difference across the spectrum must vary slowly enough that the phase difference is essentially constant during the measurement time period.

The intensity observed on a detector at the output of an interferometer is dependent on the phase difference achieved in the two paths. When light propagates a distance, z, the phase, ($\Phi$), gained across the spectrum can be described as a linear ramp with respect to k, the wavenumber in the medium traversed ($\Delta\Phi = k \cdot z$) where $k \sim 1/\lambda$. Restated: When light traverses a distance in the sample, the short wavelengths gain more phase than the long wavelengths do. If light in the two arms of the interferometer travels the same distance, it acquires the same phase ramp. If the interference of these two beams is observed on a spectrally resolved detector, a constant intensity is observed across the spectrum. A modulated interference is not observed because the phase difference between the two arms is constant. Now for example, consider light that has traveled a shorter distance in one arm, and has therefore acquired a less steep phase ramp. If the interference of these two beams is observed on a detector, a sinusoid of intensity is observed across the spectrum, because the phase difference varies linearly across the spectrum. Matching the distances in the two arms ensures that difference in the two phase ramps is not so large that the sinusoid is of too high a frequency to be observed.

Other ways exist to introduce a phase ramp across the spectrum. For example, the commonly used 'Fast-Fourier-Domain Delay Line' or 'Rapid Scanning Optical Delay Line' introduced a variable phase ramp on the reference path by spreading the spectrum with a diffraction grating, and then reflecting it off of a minor with a changing angle. The effect was to change the phase of short wavelengths to a relatively high extent, while changing the phase of long wavelengths relatively little. By this mechanism, the phase ramps of the two arms could be matched (for a particular depth in the tissue) and a deep time domain scan could be achieved with little translation of a minor surface. The structure of the Fast Fourier Domain Delay line was largely borrowed from prismatic or grating implementations of the pulse stretcher—compressor designs used for amplifying short pulse lasers. A similar Fourier Domain Delay line was developed for use with time domain OCT using a pair of stretched chirped fiber Bragg gratings.

A Bragg grating is a reflective optical device created by introducing many small reflections distributed through a volume which interfere constructively to create a precisely tuned reflectivity. The chirped Bragg grating introduces an arbitrary phase delay structure in a reflected beam by effectively making each point along the length of the structure reflective to a different wavelength. A fiber Bragg grating (FBG) is a reflective structure created within the volume of an optical fiber by introducing index of refraction variation along its length, often by exposing the glass to patterned ultraviolet radiation. Chirped fiber Bragg gratings, in which the grating period has a linear variation, are commonly used in short pulse amplification as well as dispersion compensation in optical communication networks. Bragg gratings may also be created in bulk optic materials, and in other waveguide structures, such as silicon planar waveguides, which are commonly used in integrated optical components. Bragg gratings may also be created by dynamic modulation, such as within an acousto-optic modulator.

The 'common path' or Fizeau interferometer configuration has the advantage in optical coherence tomography (OCT) that there is very little opportunity for polarization or dispersion mismatch between the arms of the interferometer. With a traditional Fizeau interferometer used in frequency domain OCT, the distance between the reference surface and the imaged surface determines the frequency of modulation across the spectrum that is detected. As the distance becomes larger, the modulation frequency increases. The spectrum modulation frequency is an important factor in the design of an OCT system, determining the number of detector elements required in spatially encoded frequency domain (spectral domain) OCT system, and the temporal detection frequency required in a time encoded (swept source) frequency domain OCT system. The difficulty in placing the reference surface at an ideal distance relative to the biological sample, due to mechanical constraints, is an important drawback that prevents the Fizeau configuration from being used in many instances. The invention described herein proposes a solution which allows a Fizeau interferometer topology, with a physical reference structure that can be located a relatively large distance away from an imaged surface, while keeping spectral modulation frequency at a measurably low rate.

SUMMARY

The present invention proposes to use a chirped Bragg grating as a reference 'surface' in a Fizeau interferometer configuration. The chirp is structured such that the long wavelengths are reflected after traversing a short distance, while shorter wavelengths are reflected after traversing a long distance. The chirped grating introduces a phase ramp across the spectrum that is much greater than would be achieved if the light were reflected by a simple reflector at the maximum extent of the grating. The grating allows one to use a comparatively short reference arm in a Fizeau interferometer while maintaining close to zero delay interference conditions.

DETAILED DESCRIPTION

Figure 1:
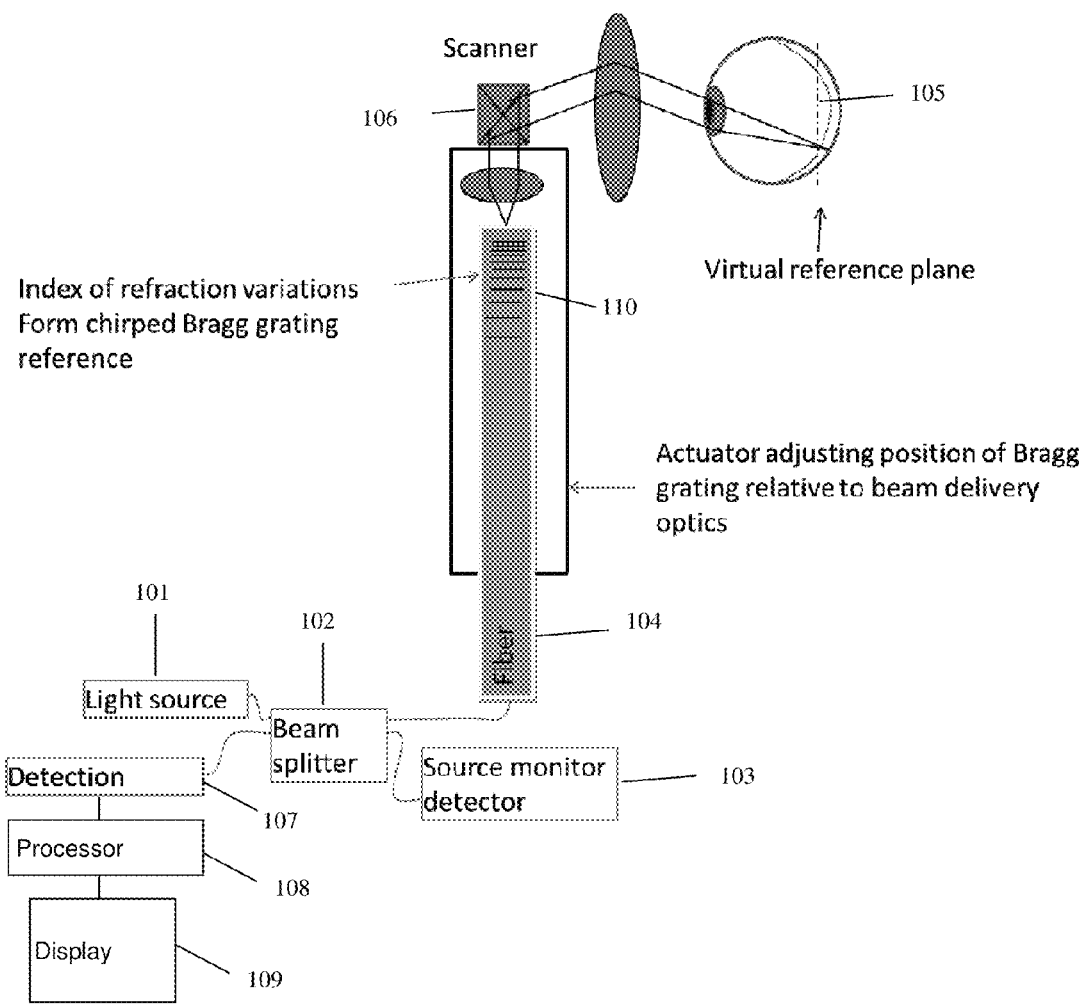
FIG. 1 illustrates an OCT system of a preferred embodiment of the present invention.

The present invention uses a chirped Bragg grating to create a reference 'surface' in a Fizeau interferometer configuration as diagrammed in FIG. 1. While the embodiment in the figure is directed towards an ophthalmic optical coherence tomography (OCT) imaging system, the invention described herein could be applied to any type of OCT system. The OCT device should be interpreted broadly to include forms of white light interferometry allowing a relatively static reference arm, including but not limited to spectral domain OCT (SD-OCT, SE-FD-OCT), and optical frequency domain imaging ('swept-source' OCT, SS-OCT, TE-FD-OCT). The device should be construed to contain all necessary computers, drive electronics, processors, display commonly understood to be necessary to achieve the diagnostic or guidance function provided by the device.

Referring to FIG. 1, light is provided by source 101. The source may be either a broad bandwidth source for SE-FD-OCT, or a swept source for TE-FD-OCT. In the case of TE-FD-OCT, the source must have sufficient coherence length to produce observable interference at the distance between the proximal end of the grating and the most distant portion of the sample to be observed. The light is split by a beam splitter 102 with one portion directed to the optical path leading to the sample, and the remaining portion optionally directed to a source monitor detector 103 for monitoring the source. The fiber beamsplitter shown in the preferred embodiment represents only an efficient means to do this with state of the art components. Optical circulators or free space optics could be used to perform a similar function.

In the illustrated embodiment, the optical path leading to the sample includes an optical fiber 104. A chirped Bragg grating 110 is formed in fiber 104 near the distal end thereof. The chirp of the grating is structured such that portions of the long wavelengths of the source are reflected after traversing a short distance in the fiber, while portions of the shorter wavelengths of the source are reflected after traversing a longer distance in the fiber. In this way the chirp is structured similarly to a classical pulse stretcher, with an important difference that the phase ramp is intended to be approximately linear. The chirped grating introduces a phase ramp across the spectrum that is much greater than would be achieved if the light were reflected by a simple reflector at the maximum extent of the grating. This reduces the rate at which the phase changes over the spectrum, thereby reducing the demand for very high density or, high speed detection electronics given a relatively large delay between the sample and reference. While the reflections are actually occurring within the fiber, the phase change in the reference light is equivalent to the change that would occur if the light were reflected at a 'virtual reference plane' placed near the sample.

Figure 2:
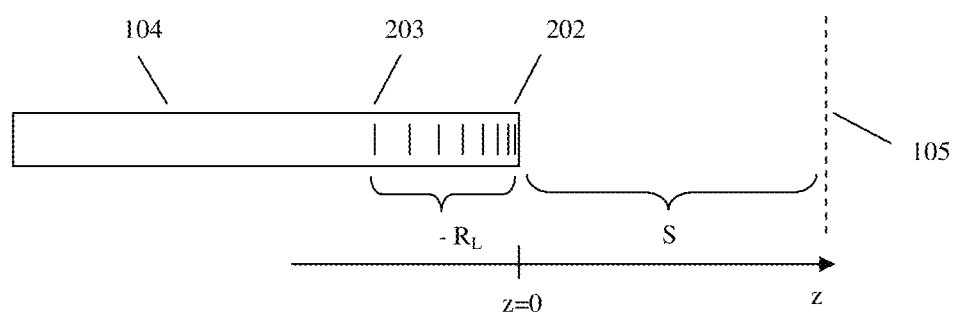
FIG. 2 illustrates the relationship between the Chirped Bragg grating and the virtual reference plane locations.

The effective length of the chirped grating is proportional to the length one would like the virtual reference plane 105 projected beyond the end of the grating depending on the type of imaging or sample under investigation. Referring to FIG. 2, suppose the short wavelength reflecting end of the grating 202 is located at position $R_s$ (near the end of the fiber 104 closest to the sample), the long wavelength reflecting end 203 of the grating is located at distance $R_L$ from the short wavelength reflecting end (closer to the source), and the virtual reference plane 105 is located at an optical path length, S, beyond the short wavelength reflecting end. (The ends of the gratings are actually the points at which the reflected wavelengths appear to come, and are approximated by the ends of the physical grating.) The end-to-end phase difference accumulated in the sample arm across the spectrum ($\Delta\Phi_{Ts}$) from short wavelength ($\lambda_s$) to long wavelength ($\lambda_L$) is defined as:

$$\Delta\Phi_{Ts}=2\pi(S/\lambda_s-S/\lambda_L)$$

Similarly, the end-to-end phase difference accumulated in the reference arm from short wavelength ($\lambda_s$) to long wavelength ($\lambda_L$) is defined as:

$$\Delta\Phi_{Tr}=2\pi(R_s/\lambda_s-R_L/\lambda_L).$$

By defining the short wavelength reflecting portion of the grating at position 0, the phase acquired by $\lambda_s$ will be zero, resulting in:

$$\Delta\Phi_{Tr}=2\pi(0-R_L/\lambda_L).$$

We wish to achieve the same end to end phase difference, $\Delta\Phi_T$, in both the sample and the reference arms:

$$\Delta\Phi_T=\Delta\Phi_{Ts}=\Delta\Phi_{Tr}.$$

Solving for $R_L$ in the equation for $\Delta\Phi_{Tr}$ yields:

$$R_L=-\Delta\Phi_T*\lambda_L/2\pi.$$

Substituting in the equation for the phase difference in the sample arm for $\Delta\Phi_T$ since all phase differences are equal:

$$R_L=-\lambda_L*(S/\lambda_s-S/\lambda_L).$$

Simplifying the equation:

$$R_L=-S*(\lambda_L/\lambda_s-1).$$

The negative value of $R_L$ indicates that the long wavelength reflecting end of the grating should be further away from the virtual reference plane than the short wavelength reflecting end. If the grating is designed to impose a linear phase ramp, it will achieve the correct phase difference (i.e. the same one as in the sample arm) for any pair $\lambda_1, \lambda_2$ within the wavelength band between $\lambda_L$ and $\lambda_S$. For a typical system $\lambda_L$=885 nm, $\lambda_s$=795 nm, the path length of the Bragg grating is about 11% of the path length of the sample arm beyond the grating. Supposing the fiber has an index of about 1.4 and the sample arm has a path length about 100 mm, the fiber grating length would be about 8 mm. Note that if a longer grating is desired, such as to increase the reflectivity or for other manufacturing purposes, the distance to the sample should be increased, and may be achieved by moving the grating down the fiber towards the source.

In additional embodiments of the invention, some flexibility in the position of the reference plane relative to the sample may be achieved by various methods, as might be desired for example to compensate for eyes of variable length or to image at different depth locations within a sample. One simple method may include a mechanism to adjust the distance between the Bragg grating and the beam delivery optics 106. Other methods may include changing properties of the Bragg grating. The effective periodicity of the grating may be changed by changing the physical spacing of the index variations within the grating and/or by changing the index of refraction of the medium in which the grating is inscribed. For example a fiber Bragg grating may be stretched, changing both its physical length and introducing stress modulation of optical index. This can be achieved by stretching the fiber section with the grating coiled around a piezo-electric material. Also piezo-electric coatings around the fiber have been demonstrated to modulate the grating structure. The index of the medium in which a Bragg grating in a silicon planar waveguide is written may be modified by adjusting the injection current in the region. Changing the temperature of a Bragg grating material has also been demonstrated to tune a grating.

Note that while the phase ramp is intended to be primarily linear, arbitrary phase dispersion can be added if desired by proper design of the Bragg grating as is known by those skilled in the art. Such phase dispersion may be added to compensate for dispersion in the sample arm, or because there are advantages to having higher order dispersion mismatch between the two arms.

The method described herein provides a means to create a reference reflection which has the advantages of the common path configuration including very little opportunity for fiber in the difference path to create polarization variability. Additionally, the reference can be precisely controlled for dispersion mismatch. The reference can be made very compact, which is advantageous particularly for surgical or diagnostic devices which must be handheld, or placed into small spaces such as an artery or the inside of a product to be inspected. Because the entire reference arm is inscribed into a piece of optical fiber, or integrated waveguide structure, this implementation also has the potential to reduce cost.

The resulting interference between the light reflected from the sample and the reference light reflected from the chirped Bragg grating is combined at beamsplitter 102 and directed to detector 107. The detection may be a simple detector in the case of TE-FD-OCT or may include a spectrometer array in the case of SE-FD-OCT. In the case of SE-FD-OCT, the optical resolution of the spectrometer must be sufficient to achieve a coherence length to produce observable interference at the distance between the proximal end of the grating and the most distant portion of the sample to be observed. To overcome the limitation of the Fizeau interferometer, that balanced detection using the out of phase return arm of the interferometer is impossible, light sampled from the source (for example using the source monitor detector 103), which does not contain the interference information from the interferometer, but does contain the noise information from the source, may be used in balanced detection. The results can be stored in the processor 108 or displayed on display 109.

Although various embodiments that incorporate the teachings of the present invention have been shown and described in detail herein, those skilled in the art can readily devise many other varied embodiments that still incorporate these teachings. The structure connecting the source, detector and interferometer should be interpreted broadly to consist of a means to direct light from a source to a Fizeau interferometer, and back to a detection means. The Fizeau interferometer consists of reference reflection provided by a Bragg grating, preferably embodied in a fiber Bragg grating; and a sample reflection such as from a biological tissue or material to be inspected. The scanning and focusing means may be required in some applications where it is desired to produce an image from the white light interferogram. In these cases, means to produce a scanned beam are well understood by those skilled in the art and the variety of which cannot be described here.

The following references are hereby incorporated by reference:

U.S. Pat. No. 5,718,738 Kohnke et al "Method for making continuously chirped fiber bragg gratings"

U.S. Patent Publication No. 2010/0091265 Franz et al "Fiber optic sensor head and interferometric measuring system"

International Publication No. WO 2007/002969 Barton et al "Optical coherence tomography probe device"

A. L. Oldenburg et al "Fast-Fourier-Domain Delay Line for in vivo Optical Coherence Tomography with a Polygonal Scanner," Appl. Opt. 42, 4606-4611 (2003)

E. Choi et al "Strained Chirped Fiber Bragg Gratings Based all-fiber Variable Optical Delay Line for Optical Coherence Tomography" Optical and Quantum Electronics 37(13-15) 1263-1276.

C. Yang et al "Amplification of optical delay by use of matched linearly chirped fiber Bragg gratings," Opt. Lett. 29(7), 685-687 (2004)

C Caucheteur et al "All fiber tunable optical delay line" Optics Express 18(3) 3093-3100

A. R. Tumlinson et al "Endoscope-tip interferometer for ultrahigh resolution frequency domain optical coherence tomography in mouse colon," Opt. Express 14, 1878-1887 (2006)

U. Sharma et al "All-fiber common-path optical coherence tomography: sensitivity optimization and system analysis," IEEE J. Sel. Top. Quantum Electronics. 11, 799-805 (2005).

A. L. Oldenburg et al "Fast-Fourier-Domain Delay Line for in vivo Optical Coherence Tomography with a Polygonal Scanner," Appl. Opt. 42, 4606-4611 (2003)

K. M. Tan et al, "In-fiber common-path optical coherence tomography using a conical-tip fiber," Opt. Express 17, 2375-2384 (2009)

B. Hofer et al "Dispersion encoded full range frequency domain optical coherence tomography," Opt. Express 17, 7-24 (2009)

What is claimed is:

1. An optical coherence tomography (OCT) system, said OCT system comprising:
   a light source arranged to generate a beam of radiation;
   an optical path for transmitting the beam from the source to a sample, said path including an elongated optical waveguide having a chirped Bragg grating reflector formed integrally with the waveguide and being located near the end of the waveguide closest to the sample and arranged for reflecting a portion of the beam prior to reaching the sample and wherein said grating reflector imparts a phase ramp to the reflected beam, said phase ramp being selected to create a virtual reference surface located beyond the end of the waveguide and closer to the sample;
   optics for scanning the portion of the beam not reflected by the grating reflector over a set of transverse locations on the sample;

a detector for measuring radiation returning from both the sample and the grating reflector, the detector generating output signals in response thereto; and a processor for converting the output signals into image data.

2. An OCT system as recited in claim 1, wherein the grating chirp is arranged so that the shorter the wavelength of light, the farther the light will travel down the optical path before being reflected.

3. An OCT system as recited in claim 1, wherein the virtual reference surface is located close to the surface of a sample.

4. An OCT system as recited in claim 1, wherein the virtual reference surface is located deep within the sample.

5. An OCT system as recited in claim 1, further comprising a path length adjustment such that the separation between the chirped Bragg grating reflector and the scanning optics may be adjusted to adjust the position of the virtual reference surface.

6. An OCT system as recited in claim 1, wherein an arbitrary phase is added to the phase ramp to compensate for the effects of dispersion in the optical path.

7. An OCT system as recited in claim 1, wherein the phase ramp created by the chirped Bragg grating reflector is adjustable.

8. An OCT system as recited in claim 7, wherein chirped Bragg grating reflector is formed in a fiber and the phase ramp is adjusted by stretching the fiber.

9. An OCT system as recited in claim 8, wherein the phase ramp is adjusted by changing the refractive index of the material used to form the chirped Bragg grating reflector.

10. An OCT system as recited in claim 1, wherein the chirped Bragg grating reflector is inscribed in the waveguide.

11. An OCT system as recited in claim 1, wherein the waveguide is an optical fiber and the chirped Bragg grating reflector is inscribed in the optical fiber.

12. An OCT system as recited in claim 1, wherein the light source is a broad bandwidth source, and the detector is a spectrograph.

13. An OCT system as recited in claim 1, wherein the source is a swept-source, and the detector is a balanced detector.

* * * * *

UNITED STATES PATENT AND TRADEMARK OFFICE
CERTIFICATE OF CORRECTION

PATENT NO.       : 8,817,269 B2                       Page 1 of 1
APPLICATION NO.  : 13/457297
DATED            : August 26, 2014
INVENTOR(S)      : Alexandre R. Tumlinson It is certified that error appears in the above-identified patent and that said Letters Patent is hereby corrected as shown below:

In the Specification

In column 2, line 18, delete "minor" and insert -- mirror --, therefor.

In column 2, line 24, delete "minor" and insert -- mirror --, therefor.

In column 4, line 30, after " $\Delta\Phi_{Ts}=2\pi(S/\lambda_s - S/\lambda_L)$ " insert -- . --.

In column 4, line 40, delete "0=$R_L/\lambda_L$" and insert -- 0-$R_L/\lambda_L$ --, therefor.

Signed and Sealed this
Twenty-fourth Day of February, 2015

Michelle K. Lee
*Deputy Director of the United States Patent and Trademark Office*